United States Patent
Furrer et al.

(10) Patent No.: US 12,384,742 B2
(45) Date of Patent: Aug. 12, 2025

(54) ORGANIC COMPOUNDS

(71) Applicant: Givaudan SA, Vernier (CH)

(72) Inventors: Stefan Michael Furrer, Cincinnati, OH (US); Adri De Klerk, Made (NL); Abdelmajid Kaouas, Utrecht (NL); Jay Patrick Slack, Cincinnati, OH (US); Cornelis Winkel, Bussum (NL)

(73) Assignee: Givaudan SA, Vernier (CH)

( * ) Notice: Subject to any disclaimer, the term of this patent is extended or adjusted under 35 U.S.C. 154(b) by 357 days.

(21) Appl. No.: 17/641,468

(22) PCT Filed: Sep. 29, 2020

(86) PCT No.: PCT/EP2020/077221
§ 371 (c)(1),
(2) Date: Mar. 9, 2022

(87) PCT Pub. No.: WO2021/063942
PCT Pub. Date: Apr. 8, 2021

(65) Prior Publication Data
US 2022/0332675 A1   Oct. 20, 2022

Related U.S. Application Data

(60) Provisional application No. 63/074,490, filed on Sep. 4, 2020, provisional application No. 62/908,177, filed on Sep. 30, 2019.

(51) Int. Cl.
 C07C 233/11 (2006.01)
 A23L 27/00 (2016.01)
 A23L 27/20 (2016.01)
(52) U.S. Cl.
 CPC .......... *C07C 233/11* (2013.01); *A23L 27/204* (2016.08); *A23L 27/88* (2016.08)
(58) Field of Classification Search
 CPC ............................ C07C 233/11; A23L 27/88
 See application file for complete search history.

(56) References Cited

U.S. PATENT DOCUMENTS

| | | | |
|---|---|---|---|
| 9,894,921 B2 | 2/2018 | Backes et al. | |
| 2012/0308703 A1 | 12/2012 | Ley et al. | |
| 2015/0272185 A1 | 10/2015 | Backes et al. | |

FOREIGN PATENT DOCUMENTS

| | | | |
|---|---|---|---|
| EP | 1291342 A1 | 3/2003 | |
| EP | 1312268 A1 | 5/2003 | |
| EP | 1642886 A2 | 4/2006 | |
| JP | 2008079557 A | * | 4/2008 |
| WO | 2003088768 A1 | 10/2003 | |
| WO | 2005015158 A2 | 2/2005 | |
| WO | 2006003107 A1 | 1/2006 | |
| WO | 2011004016 A1 | 1/2011 | |
| WO | 2013000673 A1 | 1/2013 | |
| WO | 2014083202 A1 | 6/2014 | |
| WO | 2014095564 A1 | 6/2014 | |
| WO | 2019063069 A1 | 4/2019 | |

OTHER PUBLICATIONS

International Search Report for Application No. PCT/EP2020/077221 dated Jan. 15, 2021.
Written Opinion for Application No. PCT/EP2020/077221 dated Jan. 15, 2021.
Great Britain Search Report for Application No. 1915175.2 dated Apr. 21, 2020.
Akira Inada, et al., Three putrescine bisamides from the leaves of Aglaia grandis, Phytochemistry, 2000, pp. 1091-1095, vol. 53, Elsevier Science Ltd.
Richard Detterbeck, et al., Synthesis and structure elucidation of open-chained putrescine-bisamides from Aglaia species, Tetrahedon, 2002, pp. 6887-6893, vol. 58, Elsevier Science Ltd.
Jente Boonen, et al., Alkamid database: Chemistry, occurrence and functionality of plant N-alkylamides, Journal of Ethnopharmacology, May 30, 2012, pp. 563-590, vol. 142, Elsevier Science Ltd.

* cited by examiner

*Primary Examiner* — Changqing Li
(74) *Attorney, Agent, or Firm* — Curatolo Sidoti & Trillis Co., LPA; Salvatore A. Sidoti; Floyd Trillis, III

(57) ABSTRACT

The use of compounds according to formula (I)

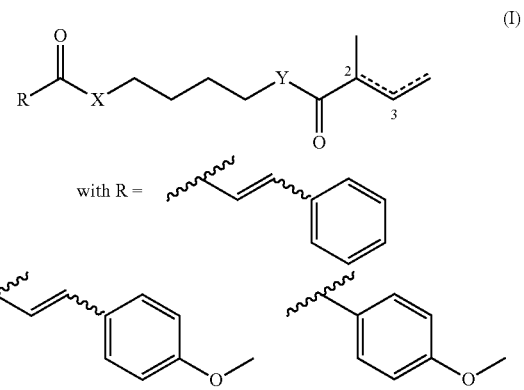

and with X, Y=—NH— or —O—, wherein at least X or Y is —NH—,
in the form of any one of its stereoisomers or a mixture thereof, wherein
~~~~~ is indicating a carbon-carbon single or double bond, and wherein one carbon-carbon double bond is present either at C2 or C3,
the wavy bond is indicating an unspecified configuration of the adjacent double bond, as umami tastant.

10 Claims, No Drawings

ORGANIC COMPOUNDS

CROSS REFERENCE TO RELATED APPLICATIONS

This application is a national stage application of International Application No. PCT/EP2020/077221, filed 29 Sep. 2020, which claims the benefit of the filing date of U.S. Provisional Patent Application No. 63/074,490, filed 4 Sep. 2020, and U.S. Provisional Patent Application No. 62/908,177, filed 30 Sep. 2019, all of which applications are incorporated herein by reference.

The present invention is directed to umami flavor and methods to create it. It relates to compounds providing umami taste and savoury flavour, and to their use in compositions and consumable products.

Umami is a flavour sensation generally associated with Asian cuisine. It has been described as savory or meaty and is characteristic of broths and cooked meats. Furthermore, improved umami taste helps make low salt products more palatable. Umami flavour has traditionally been achieved by the addition of monosodium glutamate (MSG) to foodstuffs. However, some consumers are believed to be adversely affected by glutamate salts, in particularly MSG, and consequently there remains a need for compounds that are not based on glutamate to replace or reduce reliance on such compounds for modifying the umami taste and savoury flavour of consumable products.

Amides of cinnamic acid derivatives and aromatic amines from natural sources have been reported as natural or nature-identical umami tastants in US2012308703A1, WO2013000673A1 or WO2014083202A1. Flavour compositions comprising such amides and further substances are disclosed in WO2014095564A1. A particular class of cinnamides that might generate a trigeminal effect is subject of recently published WO2019063069A1.

It has now been surprisingly found that certain putrescine bisamides and amide ester analogues, namely those of putrescine (butane-1,4-diamine) and 4-aminobutan-1-ol having for example moieties of cinnamic acid, cinnamic acid derivatives, or 4-methoxybenzoic acid on one hand, and tiglic acid ((2E)-2-methylbut-2-enoic acid) on the other hand, can be used as umami tastants.

So in a first aspect of the invention, there is provided the use of certain putrescine bisamides and amide ester analogues as ingredients to confer, enhance, improve or modify the umami taste of a consumable composition.

There is further provided a flavour composition, comprising flavour ingredients and certain putrescine bisamides or amide ester analogues.

There is further provided a consumable composition having umami flavour, said umami flavour being at least partially provided by the presence therein of certain putrescine bisamides or amide ester analogues.

In a further aspect of the invention, there are provided novel putrescine bisamides and amide ester analogues.

In a first aspect of the invention, there is provided the use of one or more compounds according to formula (I)

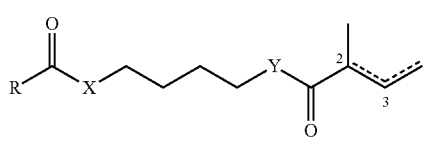

(I)

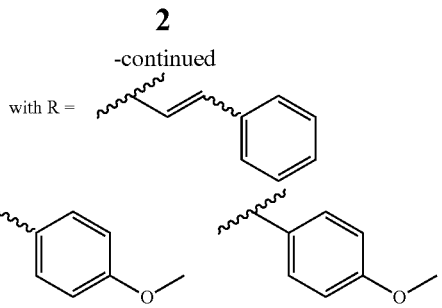

and with X, Y=—NH— or —O—, wherein at least X or Y is —NH—, in the form of any one of its stereoisomers or a mixture thereof, wherein ~~~~~~~ is indicating a carbon-carbon single or double bond, and wherein one carbon-carbon double bond is present either at C2 or C3, the wavy bond is indicating an unspecified configuration of the adjacent double bond, as an ingredient to confer, enhance, improve or modify the umami taste of a consumable composition.

In an embodiment of the present invention, there is provided the use of one or more compounds according to formula (II)

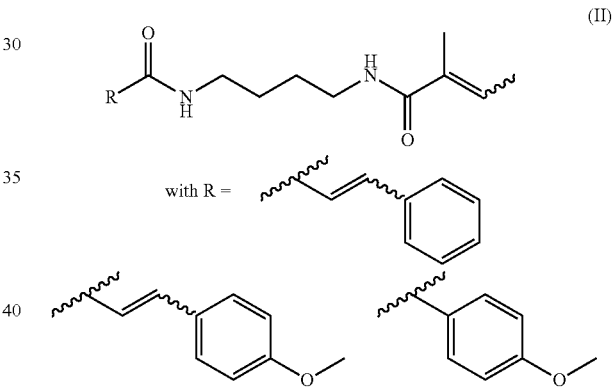

(II)

in the form of any one of its stereoisomers or a mixture thereof, wherein the wavy bond is indicating an unspecified configuration of the adjacent double bond, as an ingredient to confer, enhance, improve or modify the umami taste of a consumable composition.

Compounds according to formula (II) are bisamides and correspond to compounds according to formula (I), wherein X and Y are —NH—, and wherein the one carbon-carbon double bond is present at C2.

In a further embodiment of the present invention, there is provided the use of a compound according to formula (I) as defined above, wherein the compound is selected from the group consisting of (E)-N-(4-cinnamamidobutyl)-2-methylbut-2-enamide, (E)-N-(4-((E)-3-(4-methoxyphenyl)acrylamido)butyl)-2-methylbut-2-enamide, (E)-4-methoxy-N-(4-(2-methylbut-2-enamido)butyl)benzamide, 4-cinnamamidobutyl (E)-2-methylbut-2-enoate, 4-cinnamamidobutyl 2-methylbut-3-enoate and 4-((E)-2-methylbut-2-enamido)butyl cinnamate.

In a further embodiment of the present invention, there is provided the use of a mixture of compounds according to formula (I) as defined above. More particularly, there is provided the use of a mixture of 4-cinnamamidobutyl (E)-2-methylbut-2-enoate and 4-cinnamamidobutyl 2-methylbut-3-enoate in a ratio 1:2.

In a further embodiment of the present invention, there is provided the use of a compound according to formula (II) as defined above, wherein the compound is selected from the group consisting of (E)-N-(4-cinnamamidobutyl)-2-methylbut-2-enamide, (E)-N-(4-((E)-3-(4-methoxyphenyl)acrylamido)butyl)-2-methylbut-2-enamide and (E)-4-methoxy-N-(4-(2-methylbut-2-enamido)butyl)benzamide.

There is further provided an umami flavour composition comprising one or more compounds according to formula (I) or according to formula (II) and one or more further flavour ingredients.

The compound according to formula (I) or according to formula (II) may be used alone as the sole flavour component in a consumable composition or in combination with further flavour ingredients to provide a flavour composition ready for addition to a consumable composition. The further flavour ingredients may include other umami tastans and/or umami taste or savoury flavour enhancers, including MSG. The use of the compound according to formula (I) or according to formula (II) allows a considerable reduction in MSG levels, and in some cases the complete elimination of MSG.

Said other umami tastans and/or said umami taste or savoury flavour enhancers include, but are not limited to: L-Glu (glutamic acid, glutamate, for example in the form of its salts such as monosodium glutamate, monopotassium glutamate, monoammonium glutamate, calcium diglutamate, magnesium diglutamate), L-Asp (L-asparagine, or a salt thereof), 5'-ribonucleotides or their salts including, without limitation, calcium 5'-ribonucleotides, disodium 5'-ribonucleotides, and dipotassium 5'-ribonucleotides (e.g. inosinic acid, guanylic acid, adenosinic acid, inosinates, guanylates, and adenylates, including guanosine 5'-monophosphate, inosine 5'-monophosphate, and 5-adenylate and their salts such as disodium guanylate, disodium inosinate, disodium adenylate; dipotassium guanylate, dipotassium inosinate, dipotassium adenylate, calcium guanylate, calcium inosinate, calcium adenylate), maltol, ethyl maltol, glycine, L-leucine, autolyzed or hydrolyzed proteins (e.g. autolyzed yeast, hydrolyzed yeast, hydrolyzed vegetable proteins), Koji-Aji (a nucleotide-rich yeast extract, with fermented wheat gluten and maltodextrin also containing glutamates produced by Ajinomoto Food Ingredients), and natural preparations or extracts containing one or more of the above, for example including extracts, purees or concentrates of vegetables (including mushrooms, shiitake, soy, tomato, potato, whey, kelp/seaweeds), cereals, meat, fish (e.g. shellfish, masago), milk, cheese, and egg yolks, derived from the relevant ingredient in fresh or in fermented, partially or fully hydrolyzed form (e.g. various hydrolysed proteins).

Particular examples of said other umami tastans and/or said umami taste or savoury flavour enhancers include the compounds described in UK patent application No. 0913804 and International Application No. PCT/EP2010/059916. Other non-limiting examples of umami flavour-conferring and -enhancing compounds include those described in EP 1642886, WO 2006/015158, EP 1312268, WO 2003/088768, EP 1291342 and WO 2006/003107, all of which references are incorporated herein by reference.

Other further flavour ingredients, besides other umami tastans and/or umami taste or savoury flavour enhancers, that might be used in combination with the compound according to formula (I) or according to formula (II) to provide a flavour composition may be selected from natural flavours, artificial flavours, spices, seasonings, and the like, synthetic flavour oils and flavour aromatics and/or oils, oleoresins, essences, distillates, and extracts derived from plants, leaves, flowers, fruits, and so forth, Generally, any flavour or food additive such as those described in Chemicals Used in Food Processing, publication 1274, pages 63-258, by the National Academy of Sciences, can be used. This publication is incorporated herein by reference.

The compound according to formula (I) or according to formula (II) may be employed directly to the consumable composition or it may form a part of a flavour composition, in particular an umami flavor composition, which is subsequently admixed with the consumable composition. In a particular embodiment the compound according to formula (I) or according to formula (II) may be employed in amounts of about 0.001 to 100%, or 0.01-10%, more preferred 0.1-10%, even more preferred 0.5-5% by weight based on the flavor composition.

Compounds according to formula (I) or according to formula (II) can additionally be used in flavour compositions in conjunction with one or more ingredients or excipients conventionally used in flavour compositions, for example carrier materials and other auxiliary agents commonly used in the art. Suitable excipients for flavour compositions are well known in the art and include, for example, without limitation, solvents (including water, alcohol, ethanol, oils, fats, vegetable oil, and miglyol), binders, diluents, disintegranting agents, lubricants, flavour agents, coloring agents, preservatives, antioxidants, emulsifiers, stabilisers, flavour-enhancers, anti-caking agents, and the like.

Examples of such carriers or diluents for flavour compositions may be found in for example, "Perfume and Flavour Materials of Natural Origin", S. Arctander, Ed., Elizabeth, N.J., 1960; in "Perfume and Flavour Chemicals", S. Arctander, Ed., Vol, I & II, Allured Publishing Corporation, Carol Stream, USA, 1994; in "Flavourings", E. Ziegler and H. Ziegler (ed.), Wiley-VCH Weinheim, 1998, and "CTFA Cosmetic Ingredient Handbook", J. M. Nikitakis (ed.), 1st ed., The Cosmetic, Toiletry and Fragrance Association, Inc., Washington, 1988.

Other suitable and desirable ingredients of flavour compositions are described in standard texts, such as "Handbook of Industrial Chemical Additives", ed. M, and I. Ash, 2nd Ed., (Synapse 2000).

There is further provided a consumable composition having umami flavour, said umami flavour being at least partially provided by the presence therein of a compound according to formula (I) or according to formula (II).

There is further provided a consumable composition comprising at least one compound according to formula (I) or according to formula (II), or an umami flavour composition comprising one or more compounds according to formula (I) or according to formula (II); and a product base.

The proportion of the compound according to formula (I) or according to formula (II) used in a consumable composition will depend on the nature of the use and the effect desired. For example, the proportion needed for a partial replacement of MSG will naturally be lower than that of a complete MSG replacement. The proportion may vary between wide limits, typically between 0.01 ppm and 10000 ppm by weight of a consumable composition, more particularly between 0.1 ppm and 1000 ppm, still more particularly between 1 ppm and 500 ppm or 5-50 ppm. However, these are general indications only of useful proportions, and the skilled flavourist may use proportions outside these ranges for particular effects.

By "consumable composition" is meant any composition that is taken into the mouth for ultimate spitting out or ingestion. The composition may be in any physical form, solid, liquid or gaseous. Non-limiting examples include all food products, food additives, nutraceuticals, pharmaceuticals and any product placed in the mouth including (but not limited to) chewing gum, oral care products, and oral hygiene products including but not limited to, cereal products, rice products, tapioca products, sago products, baker's products, biscuit products, pastry products, bread products, confectionery products, dessert products, gums, chewing gums, flavor or flavor-coated food/beverage containers, yeast products, baking-powder, salt and spice products, snack foods, savoury products, mustard products, vinegar products, sauces (condiments), soups, seasonings, ready-to-eat meals, gravies, nuts & nut products, processed foods, vegetable products, meat and meat products, egg products, milk and dairy products, yoghurts, cheese products, butter and butter substitute products, milk substitute products, soy products, edible oils and fat products, beverages, carbonated beverages, alcoholic drinks such as beers, wines and spirits, non-alcoholic drinks such as soft drinks or other flavoured articles, including forms requiring reconstitution including, without limitation, beverage powder, milk based beverage powder, sugar-free beverage powder, beverage syrup, beverage concentrate, coffee and tea, food extracts, plant extracts, meat extracts, condiments, gelatins, pharmaceutical and non-pharmaceutical gums, tablets, lozenges, drops, emulsions, elixirs, syrups and other preparations for making beverages, and combinations thereof.

In particular, the compound according to formula (I) or according to formula (II) is suitable for consumable compositions selected from the group consisting of savoury applications, including snacks, soups, bouillon, sauces, meat/protein and ready-to-eat-meals, amongst others.

By "product base" is meant is meant the combination of all the usual art-recognised ingredients required for the particular consumable composition.

In a further aspect of the invention, there is provided a method of providing a consumable composition having umami taste, comprising the step of adding one or more compounds according to formula (I) or according to formula (II) to the consumable composition.

In a further aspect of the invention, there is provided a compound according to formula (I)

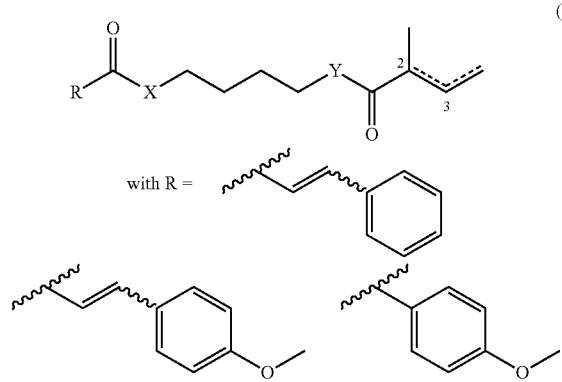

and with X, Y=—NH— or —O—, wherein at least X or Y is —NH—,
in the form of any one of its stereoisomers or a mixture thereof, wherein ⁓⁓⁓ is indicating a carbon-carbon single or double bond, and wherein one carbon-carbon double bond is present either at C2 or C3, the wavy bond is indicating an unspecified configuration of the adjacent double bond, with the proviso that the compound is not (E)-N-(4-cinnamamidobutyl)-2-methylbut-2-enamide.

In an extract of *Aglaia gracilis*, a new class of putrescine bisamides has been found (Inada et al., Phytochemistry 53, 2000, 1091-1095). Two of them have been identified as cinnamides, including (E)-N-(4-cinnamamidobutyl)-2-methylbut-2-enamide. Their synthesis has been reported (Deterbeck et al., Tetrahedron, 58 (2002) 6887-893).

In particular, the compound according to formula (I) is selected from the group consisting of (E)-N-(4-((E)-3-(4-methoxyphenyl)acrylamido)butyl)-2-methylbut-2-enamide, (E)-4-methoxy-N-(4-(2-methylbut-2-enamido)butyl)benzamide, 4-cinnamamidobutyl (E)-2-methylbut-2-enoate, 4-cinnamamidobutyl 2-methylbut-3-enoate and 4-((E)-2-methylbut-2-enamido)butyl cinnamate.

The compound according to formula (I) or according to formula (II) can be obtained using straightforward synthetic procedures and readily available starting materials known to person skilled in the art. Particular reaction conditions are further described in the examples.

The invention is now further described by the following non-limiting examples, which depict particular embodiments.

EXAMPLES

Example 1: Synthesis of (E)-N-(4-cinnamamidobutyl)-2-methylbut-2-enamide (Ia)

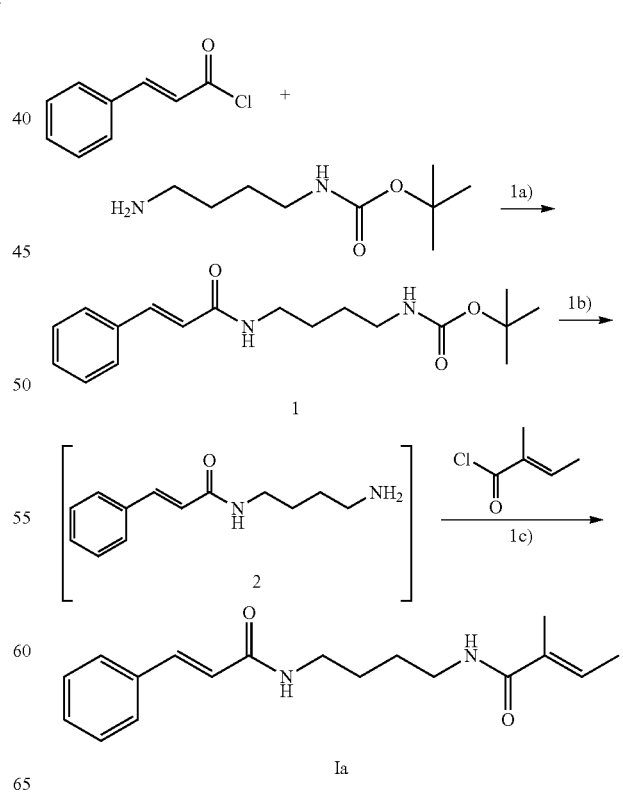

1a) tert-butyl (4-cinnamamidobutyl)carbamate (1):

A solution of cinnamoyl chloride (4.21 g, 25.3 mmol) in dichloromethane (50 ml) was added dropwise to a solution of tert-butyl (4-aminobutyl)carbamate (5 g, 26.6 mmol) and triethylamine (3.07 g, 30.4 mmol) in dichloromethane (200 ml) cooled with an ice bath. After 2 hours stirring at room temperature, the reaction mixture was washed successively with 1M HCl (2×100 ml), saturated NaHCO₃ (100 ml) and H₂O (100 ml). The organic phase was dried over MgSO₄, filtered and concentrated. The obtained solid was washed with MTBE/pentane and then dried in vacuum oven at 40° C. 7.5 g (93%) of tert-butyl (4-cinnamamidobutyl)carbamate (1) was yielded as white powder.

Purity is >95% by NMR analysis.

1H NMR (600 MHz, DMSO-d6) δ=1.15-1.58 (m, 13H), 2.82-3.00 (m, 2H), 3.08-3.23 (m, 2H), 6.55-6.70 (m, 1H), 6.77-6.92 (m, 1H), 7.29-7.47 (m, 4H), 7.49-7.66 (m, 2H), 8.03-8.32 (m, 1H) ppm.

13C NMR (151 MHz, DMSO-d6) δ=26.74, 27.26, 28.44, 38.61, 39.65, 77.52, 122.48, 127.63, 129.10, 129.54, 135.11, 138.55, 155.77, 164.96 ppm.

1b) N-(4-aminobutyl)cinnamamide (2):

TFA (4.84 ml, 62.8 mmol) was added to a solution of tert-butyl (4-cinnamamidobutyl)carbamate (1) (2 g, 6.28 mmol) in dichloromethane (100 ml). After 2 hours stirring at room temperature, the volatiles were removed at reduced pressure (till 20 mbar) at 50° C. The intermediate N-(4-aminobutyl)cinnamamide (2, N-(4-aminobutyl)-3-phenyl-prop-2-enamide) was obtained as a viscous yellow oil, which is used in the next step 1c) without any further purification.

1c) (E)-N-(4-cinnamamidobutyl)-2-methylbut-2-enamide (Ia):

The intermediate N-(4-aminobutyl)cinnamamide (2) was dissolved in dichloromethane. To the resulted solution, triethylamine (5.25 ml, 37.7 mmol) was added while stirring at room temperature. Then, a solution of (E)-2-methylbut-2-enoyl chloride (1.043 g, 8.79 mmol) in dichloromethane (10 ml) was added dropwise. Stirring was continued for two hours, and then the solution was allowed to stand at room temperature overnight. The next day, the solution was diluted with dichloromethane (100 ml) and then washed successively with diluted hydrochloric acid solution (2×100 ml) and saturated potassium carbonate solution (2×100 ml). The organic layer was separated, dried over MgSO₄, filtered and concentrated.

The obtained solid was dried in vacuum oven at 50° C./20 mbar.

1.5 g (78%) of (E)-N-(4-cinnamamidobutyl)-2-methylbut-2-enamide (Ia) was yielded as a white solid.

Purity is ca. 98% by NMR analysis,

1H NMR (600 MHz, DMSO-d6) δ=1.33-1.51 (m, 4H), 1.44 (s, 1H), 1.45 (s, 1H), 1.62-1.77 (m, 6H), 1.68 (s, 1H), 1.72 (s, 1H), 2.96-3.25 (m, 4H), 3.10 (s, 1H), 3.17 (s, 1H), 6.13-6.38 (m, 1H), 6.29 (s, 1H), 6.50-6.71 (m, 1H), 6.61 (s, 1H), 7.22-7.47 (m, 1H), 7.34-7.43 (m, 2H), 7.41 (s, 1H), 7.50-7.64 (m, 2H), 7.55 (s, 1H), 7.69-7.80 (m, 1H), 7.75 (s, 1H), 8.01-8.36 (m, 1H), 8.12 (s, 1H) ppm.

13C NMR (151 MHz, DMSO-d6) δ=12.41, 13.63, 26.73, 26.79, 38.50, 38.57, 122.34, 127.48, 128.84, 128.96, 129.40, 132.05, 134 97, 138.41, 164.81, 168.31 ppm.

Example 2: Synthesis of (E)-N-(4-((E)-3-(4-methoxyphenyl)acrylamido)butyl)-2-methylbut-2-enamide (Ib)

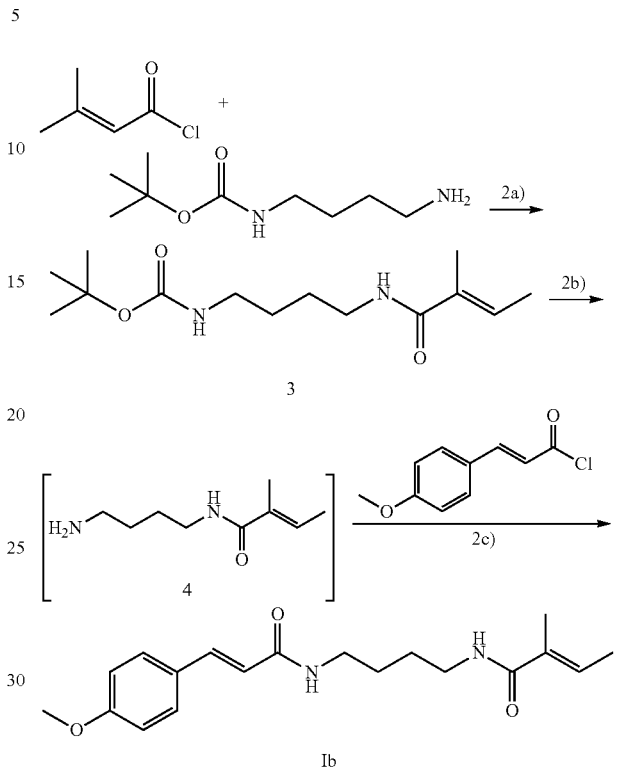

2a) tert-butyl (E)-(4-(2-methylbut-2-enamido)butyl)carbamate (3, N-Boc-N'-tiglyl-putrescine):

(E)-2-methylbut-2-enoyl chloride (3.19 g, 26.9 mmol) was added dropwise to a solution of tert-butyl (4-aminobutyl)carbamate (4.6 g, 24.43 mmol) and triethylamine (5 g, 49.4 mmol) in dichloromethane (200 mi) cooled with an ice bath. The resulted solution was stirred at room temperature for 2 hours then washed successively with 1M HCl (2×100 ml), saturated NaHCO₃ (100 ml) and H₂O (100 ml). The organic was dried with MgSO₄, filtered and concentrated. The solid was washed with pentane and then dried in vacuum oven at 40° C. 6.1 g (92%) of tert-butyl (E)-(4-(2-methylbut-2-enamido)butyl)carbamate (3) was yielded as off white solid.

Purity is >95% by NMR analysis.

2b) (E)-N-(4-aminobutyl)-2-methylbut-2-enamide (4, N-mono-tiglyl-putrescine):

TFA (8.55 ml, 111 mmol) was added dropwise to solution of tert-butyl (E)-(4-(2-methylbut-2-enamido)butyl)carbamate (3) (3 g, 11.10 mmol) in dichloro-methane (50 mi) to give a colorless solution. After 1 hour stirring at room temperature, the solution was concentrated under re-duced pressure (till 20 mbar) at 50° C. The intermediate (E)-N-(4-aminobutyl)-2-methylbut-2-enamide (4) was obtained as a viscous yellow oil, which is used in the next step 2c without any further purification.

2c) (E)-N-(4-((E)-3-(4-methoxyphenyl)acrylamido)butyl)-2-methylbut-2-enamide (Ib):

The intermediate (E)-N-(4-aminobutyl)-2-methylbut-2-enamide (4) was dissolved in dichloromethane (150 ml). To the resulted solution, triethylamine (13.47 g, 133 mmol) was added while stirring at room temperature. Then, a solution of ((E)-3-(4-methoxyphenyl)acryloyl chloride (2.62 g, 13.31 mmol) in dichloromethane (20 ml) was added dropwise. Stirring was continued for two hours and then the solution allowed to stand at room temperature overnight. The next day, the solution was diluted with dichloromethane (100 ml) and washed successively with 1M HCl (3×150 ml), saturated NaHCO₃ (2×150 ml) and H₂O (150 ml) The organic layer was dried over MgSO₄, filtered and concentrated to obtain 3.3 g of off white solid with a purity of ca. 80% by NMR analysis.

Purification by a silica gel column using DCM/ethyl acetate followed by recrystallization from ethanol resulted in 1.5 g (41%) of (E)-N-(4-((E)-3-(4-methoxyphenyl)acrylamido)butyl)-2-methylbut-2-enamide (Ib) as white solid.

Purity is >98% by NMR analysis.

1H NMR (600 MHz, DMSO-d6) δ=1.35-1.50 (m, 4H), 1.43 (s, 1H), 1.44 (s, 1H), 1.60-1.77 (m, 6H), 1.67 (s, 1H), 1.72 (s, 1H), 3.00-3.21 (m, 4H), 3.10 (s, 1H), 3.15 (s, 1H), 3.70-3.85 (m, 3H), 3.78 (s, 1H), 6.17-6.36 (m, 1H), 6.27 (s, 1H), 6.41-6.56 (m, 1H), 6.96 (d, J=8.95 Hz, 2H), 7.21-7.43 (m, 1H), 7.43-7.56 (m, 2H), 7.48 (s, 1H), 7.60-7.82 (m, 1H), 7.74 (s, 1H), 7.89-8.17 (m, 1H), 8.01 (s, 1H) ppm.

13C NMR (151 MHz, DMSO-d6) δ=12.41, 13.63, 26.79, 38.46, 38.59, 55.26, 114.38, 119.85, 127.52, 129.03, 132.05, 138.11, 160.25, 165.12, 168.32 ppm.

Example 3: Synthesis of (E)-4-methoxy-N-(4-(2-methylbut-2-enamido)butyl)benzamide (Ic)

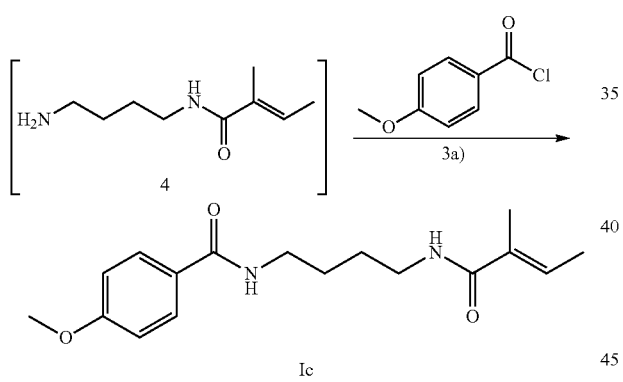

3a) The intermediate (E)-N-(4-aminobutyl)-2-methylbut-2-enamide (4) obtained from step 2b) of Example 2 was dissolved in dichloromethane (150 ml). To the resulted solution, trimethylamine (4.04 g, 39.9 mmol) was added while stirring at room temperature. Then, a solution of 4-methoxybenzoyl chloride (0.7 g, 4.10 mmol) in dichloromethane (20 ml) was added dropwise. Stirring was continued for two hours and then the solution was allowed to stand at room temperature overnight. The next day, the solution was diluted with dichloromethane (100 ml) and washed successively with 1M HCl (2×150 ml), saturated NaHCO₃ (2×150 ml) and H₂O (150 ml), The organic layer was dried over MgSO₄, filtered and concentrated to obtain a slight yellow solid, which was recrystallized from ethyl acetate, washed with ether and dried in vacuum oven at 50° C., 0.8 g (79%) of (E)-4-methoxy-N-(4-(2-methylbut-2-enamido)butyl)benzamide (Ic) was yielded as white powder.

Purity is >95% by NMR analysis.

1H NMR (600 MHz, DMSO-d6) δ=1.29-1.54 (m, 4H), 1.61-1.74 (m, 6H), 3.03-3.16 (m, 2H), 3.18-3.28 (m, 2H), 3.73-3.86 (m, 3H), 5.82-6.50 (m, 1H), 6.79-7.08 (m, 2H), 7.59-7.92 (m, 3H), 8.21-8.43 (m, 1H) ppm.

13C NMR (151 MHz, DMSO-d6) δ=12.55, 13.76, 26.96, 38.50, 38.77, 55.47, 113.55, 127.02, 128.97, 129.07, 132.18, 161.53, 165.68, 168.42 ppm.

Example 4: Synthesis of a mixture of 4-cinnamamidobutyl (E)-2-methylbut-2-enoate (Id) and 4-cinnamamidobutyl 2-methylbut-3-enoate (Ie) (1:2)

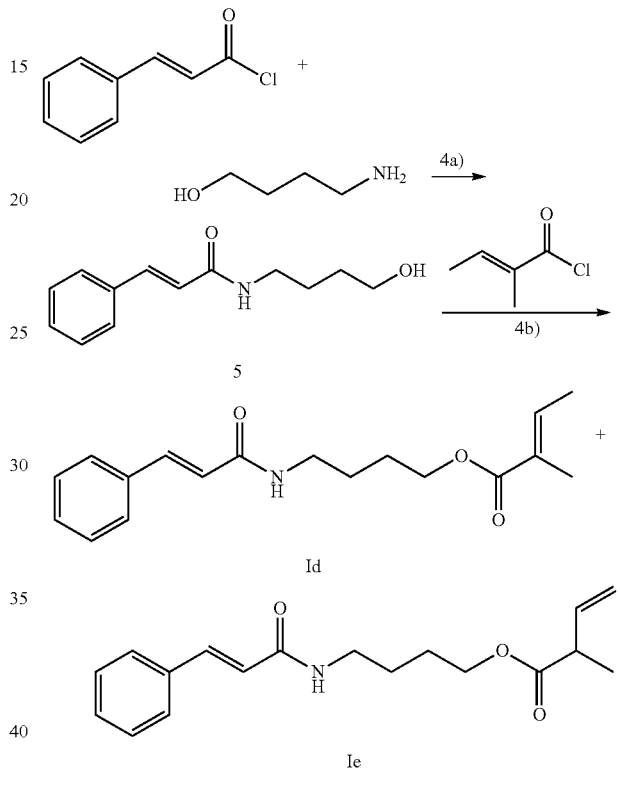

4a) N-(4-hydroxybutyl)cinnamamide (5)

In a 250 mL round-bottomed flask 4-aminobutan-1-ol (3.21 g, 36.0 mmol) and triethylamine (9.20 ml, 66.0 mmol) in dichloromethane (100 ml) were provided. Cinnamoyl chloride (5 g, 30.0 mmol) in 10 mL of dichloromethane was added dropwise while cooling with an ice/water bath. The cooling bath was removed, and stirring was continued for 2 hours at room temperature. The reaction mixture was diluted with dichloromethane and washed with a diluted hydrochloric acid solution. The organic layer was separated and washed with a saturated sodiumbicarbonate solution and brine. The organic layer was dried and evaporated to yield 4.5 g (67%) of N-(4-hydroxybutyl)cinnamamide (5) as an oil.

Purity is >95% by NMR analysis.

1H NMR (600 MHz, DMSO-d6) δ=1.35-1.55 (m, 4H), 3.09-3.25 (m, 2H), 3.36-3.58 (m, 2H), 4.43 (t, 1H), 6.61-6.64 (d, 1H), 7.32-7.43 (m, 4H), 7.54-7.56 (d, 2H), 8.11 (br t, 1H) ppm.

13C NMR (151 MHz, DMSO-d6) δ=25.89, 30.00, 38.63, 60.45, 122.38, 127.49, 128.97, 129.40, 134.99, 138.40, 164.81 ppm.

4b) 4-cinnamamidobutyl (E)-2-methylbut-2-enoate (Id) and 4-cinnamamidobutyl 2-methylbut-3-enoate (Ie)

N-(4-hydroxybutyl)cinnamamide (5) (1 g, 4.56 mmol) was dissolved in dichloromethane (25 ml). Triethylamine (1.271 ml, 9.12 mmol) was added while stirring. Then (E)-2-methylbut-2-enoyl chloride (0.595 g, 5.02 mmol) was added dropwise while stirring. The exothermic reaction started to reflux. Stirring was continued for three hours at room temperature. The reaction mixture was diluted with ether and washed with a diluted hydrochloric acid solution. The organic layer was separated and washed with a saturated sodiumbicarbonate solution, dried and concentrated. The residue was purified by flash column chromatography. Eluent dichloromethane/methanol from 0 to 3% methanol.

0.7 g of product Id and Ie (51%) was obtained in a ratio of 1:2.

1H NMR (600 MHz, DMSO-d6) δ=1.16-1.20 (m, 3H), 1.45-1.56 (m, 3H), 1.57-1.67 (m, 3H), 1.74-1.78 (m, 3H), 3.16-3.23 (m, 4H), 4.03-4.07 (m, 2H), 4.07-4.11 (m, 1H) 5.06-5.17 (m, 2H), 5.84-5.92 (m, 1H), 6.59-6.64 (m, 1H), 6.74-6.81 (m, 1H), 7.35-7.39 (m, 2H), 7.39-7.41 (m, 2H), 7.41-7.44 (m, 3H), 7.53-7.59 (m, 3H), 8.04-8.21 (m, 1H) ppm.

13C NMR (151 MHz, DMSO-d6) δ=12.50, 14.70, 18.90, 26.18, 26.24, 26.32, 38.73, 38.78, 40.56, 43.28, 64.23, 64.37, 116.48, 122.78, 128.01, 129.47, 129.92, 135.46, 137.67, 137.86, 139.00, 165.36, 174.09 ppm.

Example 5: Synthesis of 4-((E)-2-methylbut-2-enamido)butyl cinnamate (If)

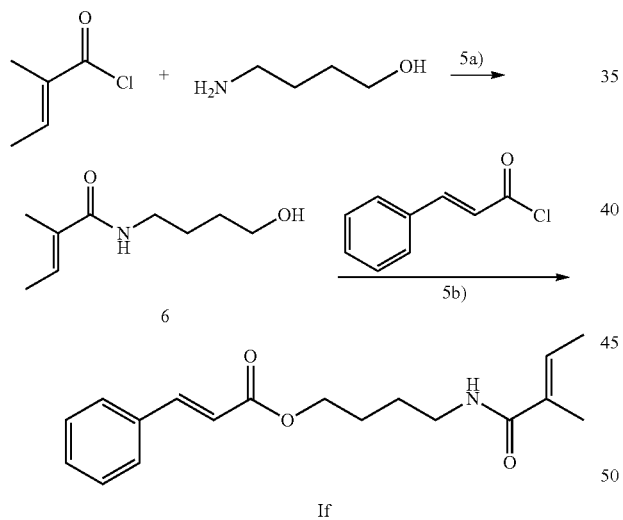

5a) (E)-N-(4-hydroxybutyl)-2-methylbut-2-enamide (6)

4-aminobutan-1-ol (3.01 g, 33.7 mmol) was dissolved in dichloromethane (50 ml). Triethylamine (4.70 ml, 33.7 mmol) was added while stirring. The solution was cooled with an ice/water bath and (E)-2-methylbut-2-enoyl chloride (2 g, 16.87 mmol) was added dropwise. The cooling bath was removed and stirring was continued for three hours at room temperature. The reaction mixture was diluted with dichloromethane and washed with a diluted hydrochloric acid solution. The organic layer was separated and washed with a potassiumcarbonate solution, dried and concentrated. The residue was purified by flash column chromatography. Eluent DCM/methanol from 0 to 3% methanol. 1 g of an oil was obtained.

Purity is >95% by NMR analysis.

1H NMR (600 MHz, DMSO-d6) δ=1.28-1.51 (m, 4H), 1.62-1.70 (d, 3H), 1.74 (s, 3H), 3.00-3.13 (m, 2H), 3.36-3.40 (m, 2H), 4.30-4.36 (t, 1H), 6.25-6.30 (q, 1H), 7.59-7.86 (br t, 1H) ppm.

13C NMR (151 MHz, DMSO-d6) δ=12.41, 13.62, 25.90, 30.02, 38.79, 60.54, 128.74, 132.11, 168.28 ppm.

5b) 4-((E)-2-methylbut-2-enamido)butyl cinnamate (If)

To (E)-N-(4-hydroxybutyl)-2-methylbut-2-enamide (6, 1 g, 5.84 mmol) was added cinnamoyl chloride (0.973 g, 5.84 mmol). The reaction mixture was stirred at 60° C. for three hours. Then it was heated at 100° C. for a short time. The crude was purified by flash column chromatography, eluent DCM/methanol with 1% methanol to yield 1.5 g of a colorless oil.

1H NMR (600 MHz, DMSO-d6) δ=1.39-1.77 (m, 10H), 3.05-3.22 (q, 2H), 4.08-4.21 (t, 2H), 6.18-6.38 (q, 1H), 6.59-6.71 (d, 1H), 7.29-7.50 (m, 3H), 7.62-7.82 (m, 4H) ppm.

13C NMR (151 MHz, DMSO-d6) δ=12.54, 13.75, 25.88, 30.86, 38.53, 63.98, 118.24, 128 34, 128.54, 129.08, 130.63, 132.17, 134.18, 144.62, 165.43, 168.48 ppm.

Example 6: Taste Evaluation—Comparison with MSG

An aqueous NaCl solution (0.5% by weight) was prepared. To this base was added:
a) 30 ppm of the compound Ia (sample 6a);
b) 200 ppm of MSG (sample 6b, benchmark).

The tastes of the two samples 6a and 6b have been evaluated by 5 trained panellists. They were asked to rate the intensity of sample 6a as difference to sample 6b and to describe the overall effect. Typically, the following descriptors are used to describe the effect: umami, salty, bitter, overall sweet.

The taste of sample 6a was described as umami, brothy and longlasting. The umami on bitter level was marked as a little higher than benchmark. Overall, sample 6a was preferred over sample 6b.

Example 7: Taste Evaluation—Comparison with Further Derivatives

An aqueous NaCl solution (0.5% by weight) was prepared. To this base was added:
a) 20 ppm of the compound Ia (sample 7a);
b) 20 ppm of the compound Ib (sample 7b):
c) 20 ppm of the compound Ic (sample 7c).

The tastes of the three samples 7a, 7b and 7c have been evaluated by 5 trained panellists.

The taste of sample 7b was described as more umami, stronger and more lingering, more sweet, but having an off note, animalic, floral sweet in comparison to sample 7a.

The taste of sample 7c was described as more umami and cleaner umami than sample 7a.

Example 8: Taste Evaluation of Amide Ester Analogues

An aqueous solution of NaCl (0.5% by weight) and MSG (0.05% by weight) was prepared.

To this base was added:
a) 20 ppm of the mixture of the compound (Id+Ie) in a ratio 1:2 (sample 8a);
b) 20 ppm of the compound If (sample 8b).

A group of four experienced tasters compared the samples 8a and 8b with the pure base.

Unanimously the group found that sample 8a was more umami than the base Additionally some bitterness was perceived.

Unanimously the group found that sample 8b was more umami than the base. The tasting was described as a pleasant taste experience.

The invention claimed is:

1. A method of using at least one compound according to formula (I):

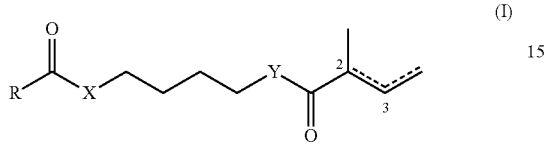

wherein R is independently selected from the group consisting of

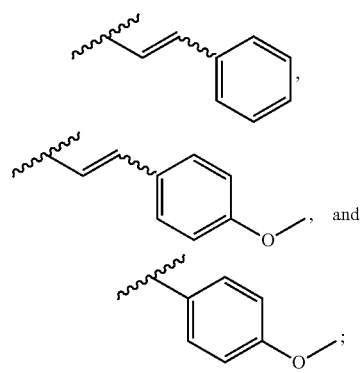

and wherein X, Y are independently —NH— or —O—, wherein at least one of X or Y is —NH—, in the form of any one of its stereoisomers or a mixture thereof, wherein ----- indicates a carbon-carbon single or double bond, and wherein one carbon-carbon double bond is present either at C2 or C3, and wherein each of the wavy bond on the right side of the double bond indicates an unspecified configuration of the adjacent double bond, and the remainder of the wavy bond indicates the linking site of the R group to C(═O)X in formula (I), as an ingredient to confer, enhance, improve, or modify the umami taste of a consumable composition, wherein the method comprises adding between 0.01 ppm and 10000 ppm by weight of said at least one compound of formula (I) to said consumable composition.

2. The method according to claim 1, wherein the at least one compound according to formula (I) is further defined by formula (II):

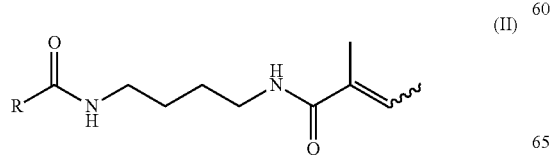

wherein R is independently selected from the group consisting of

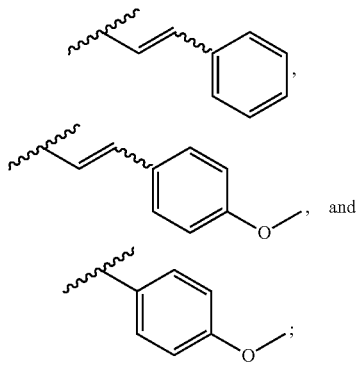

in the form of any one of its stereoisomers or a mixture thereof, and wherein the wavy bond in formula (II) indicates an unspecified configuration of the adjacent double bond, wherein for each R group each of the wavy bond on the right side of the double bond indicates an unspecified configuration of the adjacent double bond, and the remainder of the wavy bond indicates the linking site of the R group to C(═O)NH in formula (II), as an ingredient to confer, enhance, improve, or modify the umami taste of a consumable composition.

3. The method according to claim 1, wherein the at least one compound according to formula (I) is selected from the group consisting of (E)-N-(4-cinnamamidobutyl)-2-methylbut-2-enamide, (E)-N-(4- ((E)-3-(4-methoxyphenyl)acrylamido)butyl)-2-methylbut-2-enamide, (E)-4-methoxy-N-(4-(2-methylbut-2-enamido)butyl)benzamide, 4-cinnamamidobutyl (E)-2-methylbut-2-enoate, 4-cinnamamidobutyl 2-methylbut-3-enoate, and 4-((E)-2-methylbut-2-enamido) butyl cinnamate.

4. A method of providing a consumable composition having umami taste, comprising the step of adding between 0.01 ppm and 10000 ppm of at least one compound according to formula (I):

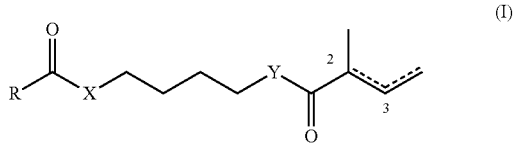

wherein R is independently selected from the group consisting of

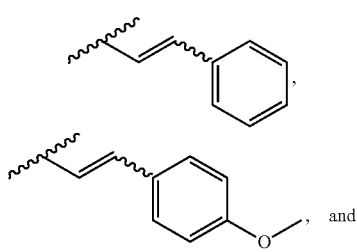

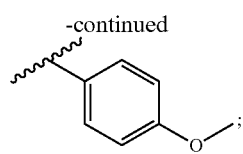

and wherein X, Y are independently —NH— or —O—, wherein at least one of X or Y is —NH—, in the form of any one of its stereoisomers or a mixture thereof, wherein ------ indicates a carbon-carbon single or double bond, and wherein one carbon-carbon double bond is present either at C2 or C3, and wherein each of the wavy bond on the right side of the double bond indicates an unspecified configuration of the adjacent double bond, and the remainder of the wavy bond indicates the linking site of the R group to C(=O)X in formula (I), to the consumable composition.

5. A compound according to formula (I)

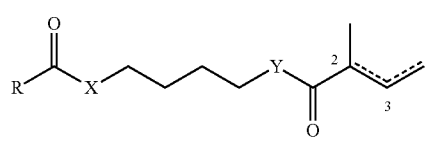

wherein R is independently selected from the group consisting of

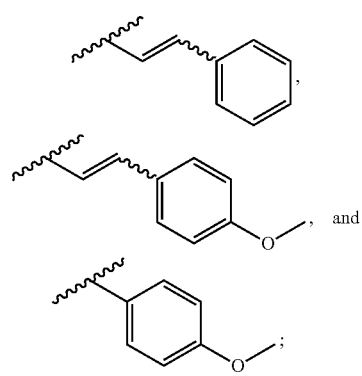

and wherein X, Y are independently —NH— or —O—, wherein at least one of X or Y is —NH—, in the form of any one of its stereoisomers or a mixture thereof, wherein ------ indicates a carbon-carbon single or double bond, and wherein one carbon-carbon double bond is present either at C2 or C3, and wherein each of the wavy bond on the right side of the double bond indicates an unspecified configuration of the adjacent double bond, and the remainder of the wavy bond indicates the linking site of the R group to C(=O)X in formula (I), with the proviso that the compound is not (E)-N-(4-cinnamamidobutyl)-2-methylbut-2-enamide.

6. The compound according to formula (I) as defined in claim 5, selected from the group consisting of (E)-N-(4-((E)-3-(4-methoxyphenyl)acrylamido)butyl)-2-methylbut-2-enamide, (E)-4-methoxy-N-(4-(2-methylbut-2-enamido)butyl)benzamide, 4-cinnamamidobutyl (E)-2-methylbut-2-enoate, 4-cinnamamidobutyl 2-methylbut-3-enoate, and 4-((E)-2-methylbut-2-enamido)butyl cinnamate.

7. A consumable composition comprising:
(i) the compound as defined in claim 5; and
(ii) a product base.

8. A consumable composition comprising:
(i) the compound as defined in claim 6; and
(ii) a product base.

9. A consumable composition comprising:
(i) at least one compound according to formula (I):

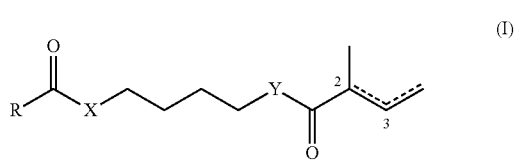

wherein R is independently selected from the group consisting of

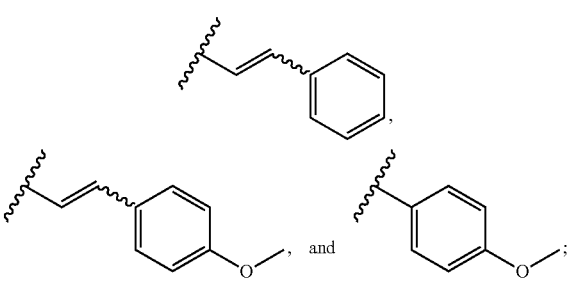

and wherein X, Y are independently —NH— or —O—, wherein at least one of X or Y is —NH—, in the form of any one of its stereoisomers or a mixture thereof, wherein ------ indicates a carbon-carbon single or double bond, and wherein one carbon-carbon double bond is present either at C2 or C3, and wherein each of the wavy bond on the right side of the double bond indicates an unspecified configuration of the adjacent double bond, and the remainder of the wavy bond indicates the linking site of the R group to C(=O)X in formula (I), wherein the at least one compound according to formula (I) comprises between 0.01 ppm and 10000 ppm by weight of the consumable composition, and (ii) a product base.

10. A consumable composition comprising:
(i) at least one compound according to formula (II)

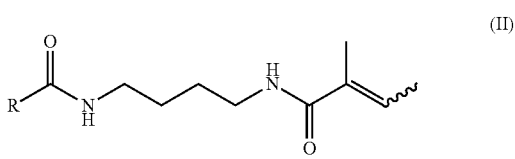

wherein R is independently selected from the group consisting of

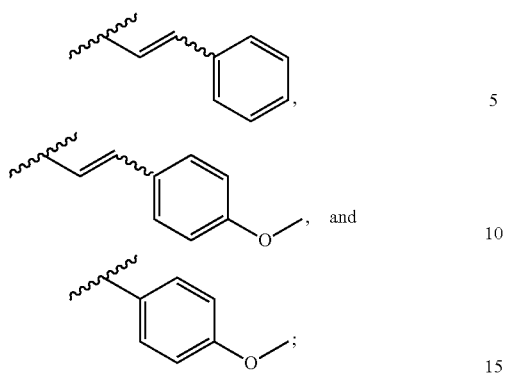

in the form of any one of its stereoisomers or a mixture thereof, and
wherein the wavy bond in formula (II) indicates an unspecified configuration of the adjacent double bond,
wherein for each R group each of the wavy bond on the right side of the double bond indicates an unspecified configuration of the adjacent double bond, and the remainder of the wavy bond indicates the linking site of the R group to C(=O)NH in formula (II), and
wherein the at least one compound according to formula (II) comprises between 0.01 ppm and 10000 ppm by weight of the consumable composition; and
(ii) a product base.

\* \* \* \* \*